US009068925B1

(12) United States Patent
Hunt et al.

(10) Patent No.: US 9,068,925 B1
(45) Date of Patent: Jun. 30, 2015

(54) OPTICAL INTERNAL CONFIGURATION MONITORING SYSTEM MONITORING THE BENDING OF A PLATFORM FOR CORRECTING TRAVEL DIRECTION OF A PLATFORM

(75) Inventors: Jeffrey H. Hunt, Thousand Oaks, CA (US); Timothy E. Bridges, Huntington Beach, CA (US)

(73) Assignee: THE BOEING COMPANY, Chicago, IL (US)

(*) Notice: Subject to any disclaimer, the term of this patent is extended or adjusted under 35 U.S.C. 154(b) by 375 days.

(21) Appl. No.: 13/534,848

(22) Filed: Jun. 27, 2012

(51) Int. Cl.
*G01J 1/04* (2006.01)
*G01N 21/17* (2006.01)

(52) U.S. Cl.
CPC ...................... *G01N 21/17* (2013.01)

(58) Field of Classification Search
USPC .............. 250/208.1, 216, 221, 222.1, 227.14, 250/227.15, 227.16, 227.17, 227.1, 8, 250/227.24, 227.28; 385/12, 13, 14, 385/100–107
See application file for complete search history.

(56) References Cited

U.S. PATENT DOCUMENTS

| 4,845,357 | A | * | 7/1989 | Brennan | 250/227.14 |
| 4,950,883 | A | * | 8/1990 | Glenn | 250/227.14 |
| 5,310,134 | A | * | 5/1994 | Hsu et al. | 244/3.12 |
| 5,927,680 | A | | 7/1999 | Bridges et al. | |

* cited by examiner

*Primary Examiner* — Georgia Y Epps
*Assistant Examiner* — Don Williams
(74) *Attorney, Agent, or Firm* — Yee & Associates, P.C.

(57) ABSTRACT

A method and apparatus for detecting a change in an internal configuration of a platform. The apparatus comprises a number of optical fibers and a detector. The number of optical fibers extends through a platform. The detector is configured to detect a change in a manner in which light propagates through the number of optical fibers when an internal configuration of the platform changes.

21 Claims, 11 Drawing Sheets

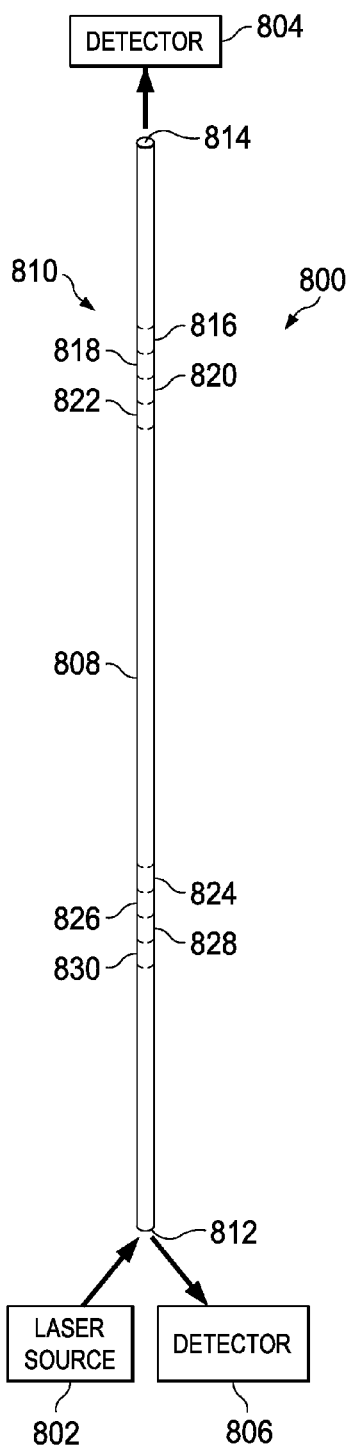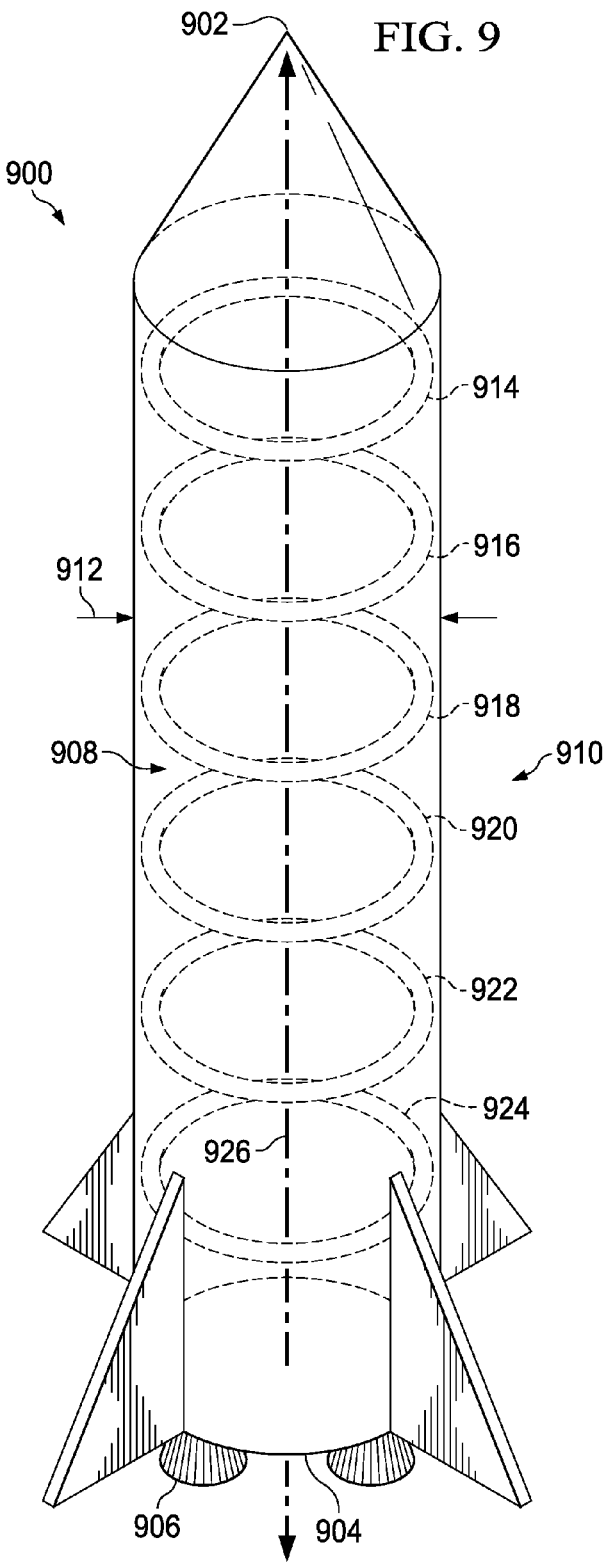

FIG. 14
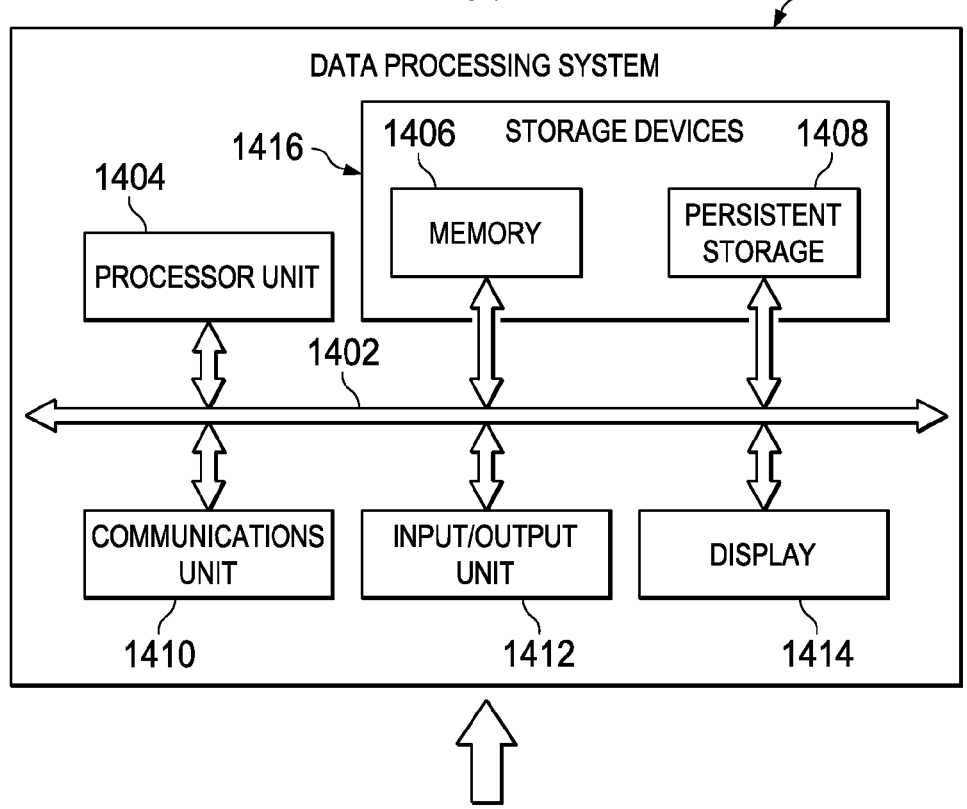
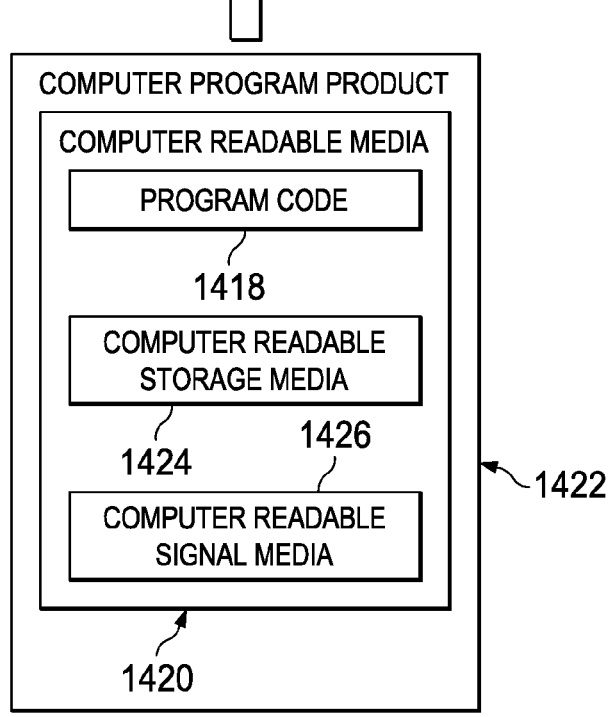

OPTICAL INTERNAL CONFIGURATION MONITORING SYSTEM MONITORING THE BENDING OF A PLATFORM FOR CORRECTING TRAVEL DIRECTION OF A PLATFORM

BACKGROUND INFORMATION

1. Field

The present disclosure relates generally to rockets and, in particular, to managing the operation of a rocket. Still more particularly, the present disclosure relates to a method and apparatus for detecting internal configuration changes that may occur during the operation of a rocket.

2. Background

A rocket is a vehicle that has a rocket engine used for thrust. For example, a rocket may be a missile, a spacecraft, an aircraft, or other vehicle that has a rocket engine.

During flight, a rocket may undergo internal configuration changes. A change to the internal configuration of a rocket is a change in the structure of the rocket. A change to the internal configuration of the rocket may include, for example, bending of the structure of the rocket along a longitudinal axis of the rocket. This type of bending may be referred to as vibrations, bending modes, and other types of changes to the internal configuration of the rocket.

These internal configuration changes may be interpreted by a navigation control system in the rocket as a change in the direction of flight of the rocket. For example, a bending along the length of the rocket may cause a change in the position of a tip of the rocket such that the rocket temporarily points the wrong direction, although the rocket is actually traveling in the correct direction.

As a result, the navigation control system may attempt to correct the direction of the rocket based on the perceived errors in the direction of travel. Performing these types of corrections when they are unnecessary may increase the fuel usage more than desired.

Further, with the use of different types of engines, performing unnecessary corrections may deplete the pressurized fluid used to steer these engines. For example, with a Vernier engine, performing unnecessary corrections may prematurely deplete the Vernier blow down fluid that is used to steer the engine. Over-corrections also may result in undesired operation of the rocket.

Currently, mechanical devices are used to identify the bending of a rocket. These mechanical devices may be part of an internal configuration detection system. For example, a gyroscope may be mounted on the rocket. The gyroscope may detect these changes and send the information about the detected changes to the navigation control system. In this manner, the navigation control system may take this information into account when controlling the direction in which the rocket travels.

Although gyroscopes may be useful, these gyroscopes are typically mounted at locations where the greatest amount of deflection occurs when the rocket bends. These locations may be inconvenient locations. For example, when the rocket takes the form of a launch vehicle, these locations may be on a fuel tank, such as a liquid oxygen fuel tank. As a result, the gyroscopes cannot be directly connected to the fuel tank. Additional mechanical devices are needed to mount the gyroscopes to provide a temperature neutral environment at these locations. Further, these additional mechanical devices also are selected to isolate the gyroscopes from vibrations and motions not related to the bending of the rocket.

As a result, this type of internal configuration detection system may be more complex, larger, heavier, and more expensive than desired. Therefore, it would be desirable to have a method and apparatus that takes into account at least some of the issues discussed above, as well as other possible issues.

SUMMARY

In one illustrative embodiment, an apparatus comprises a number of optical fibers and a detector. The number of optical fibers extends through a platform. The detector is configured to detect a change in a manner in which light propagates through the number of optical fibers when an internal configuration of the platform changes.

In another illustrative embodiment, a method for detecting a change in an internal configuration of a platform is provided. Light is sent through a number of optical fibers extending through the platform. A change in a manner in which the light propagates through the number of optical fibers is detected when the internal configuration of the platform changes.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 8 is an illustration of components that may be used in an optical internal configuration monitoring system in accordance with an illustrative embodiment;

FIG. 9 is another illustration of a rocket with an optical internal configuration monitoring system in accordance with an illustrative embodiment;

FIG. 14 is an illustration of a block diagram of a data processing system in accordance with an illustrative embodiment.

DETAILED DESCRIPTION

The illustrative embodiments recognize and take into account one or more different considerations. For example, the illustrative embodiments recognize and take into account that the use of gyroscopes to detect the internal configuration changes of a rocket may result in more complexity, space usage, weight, and cost than desired.

For example, the illustrative embodiments recognize and take into account that simulations are performed ahead of time on a rocket to identify internal configuration changes such as bending. These simulations are performed to identify locations where the most deflection occurs in a rocket. Afterwards, testing is performed with gyroscopes in those locations to determine whether those locations are the desired locations for detecting the bending of the rocket. Performing these steps requires time and money to be expended prior to building or upgrading a rocket to include gyroscopes for detecting bending in the rocket.

Further, this process is repeated for different types of rockets and even different models of the same type of rocket. Moreover, testing may be done to find the desired type of mechanical devices needed to provide the gyroscope a temperature neutral environment. These types of mechanical devices may be different for different types of rockets or may be dependent on the type of usage of the rocket. Thus, a considerable amount of effort and expense is needed prior to implementing an internal configuration detection system with a gyroscope on a rocket.

The illustrative embodiments also recognize and take into account that with currently used internal configuration detection systems, other types of internal configuration changes are not detected. For example, the illustrative embodiments recognize and take into account that an internal configuration change such as twisting of the rocket about a longitudinal axis through the rocket may not be detected using gyroscopes in the manner discussed above.

Thus, the illustrative embodiments provide a method and apparatus for detecting changes in the internal configuration of a platform. In one illustrative embodiment, an apparatus comprises a number of optical fibers and a detector. As used herein, a "number of" when used with reference to items means one or more items. For example, a number of optical fibers is one or more optical fibers.

The number of optical fibers extends through the platform such that changes in the internal configuration of the platform cause a change in the manner in which light propagates through the number of optical fibers. The detector is configured to detect changes in the manner in which light propagates through the number of optical fibers using the light sent through the number of optical fibers.

Figure 1:
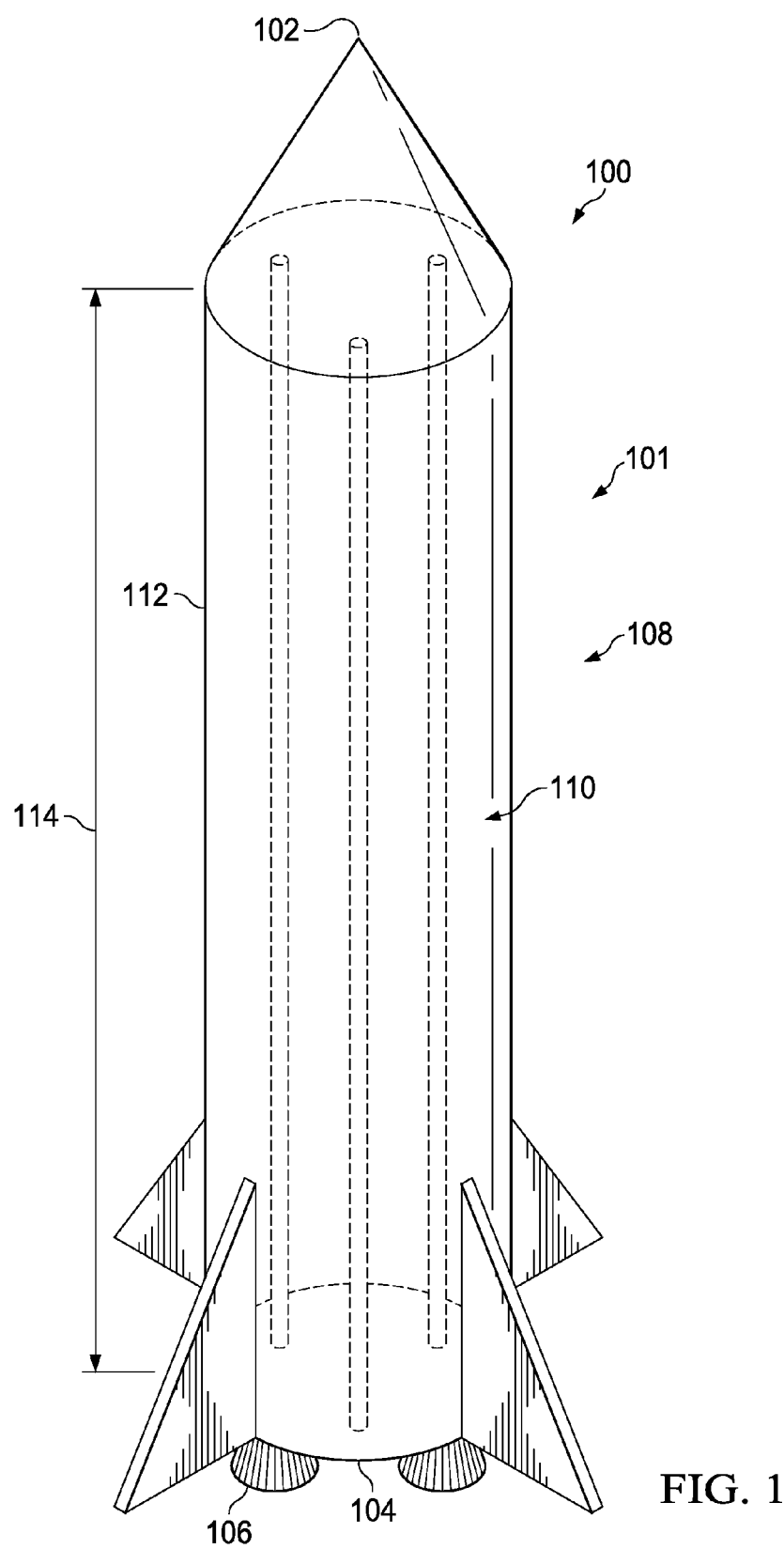
FIG. 1 is an illustration of a rocket with an optical internal configuration monitoring system in accordance with an illustrative embodiment.

With reference now to the figures, and in particular, with reference to FIG. 1, an illustration of a rocket with an optical internal configuration monitoring system is depicted in accordance with an illustrative embodiment. As depicted, rocket 100 has elongate shape 101 with first end 102 and second end 104. First end 102 is the tip of rocket 100. Rocket engines 106 are located at second end 104.

In this illustrative example, rocket 100 includes optical internal configuration monitoring system 108 to monitor for changes in the internal configuration of rocket 100. Optical internal configuration monitoring system 108 includes optical fibers 110 that extend through structure 112 of rocket 100. In this illustrative example, optical fibers 110 extend longitudinally through structure 112 along length 114 of rocket 100.

Optical fibers 110 are configured to propagate light. The propagation of light through optical fibers 110 may be detected during operation of rocket 100. When internal configuration changes such as bending of structure 112 of rocket 100 occur, the propagation of light through optical fibers 110 is affected in these illustrative examples.

This change in the propagation of light through optical fibers 110 is identified as a bending of rocket 100. This bending of rocket 100 may be taken into account when operating rocket 100 to avoid unnecessary corrections to the direction in which rocket 100 travels. In other words, detection of a bending in rocket 100 by optical fibers 110 may be taken into account by optical internal configuration monitoring system 108 to prevent a navigation system from over-correcting rocket 100. As a result, optical internal configuration monitoring system 108 may provide more accurate monitoring and navigation of rocket 100 than currently available systems.

Figure 2:
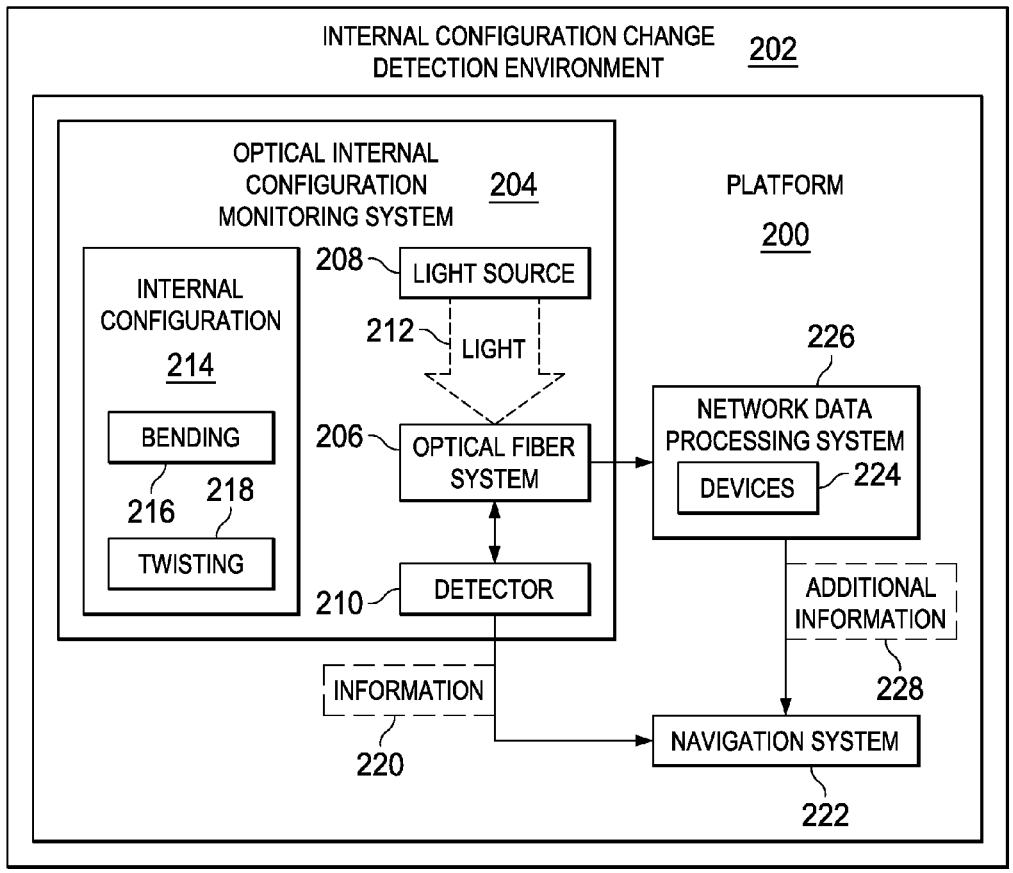
FIG. 2 is an illustration of a block diagram of an internal configuration change detection environment in accordance with an illustrative embodiment.

Turning now to FIG. 2, an illustration of a block diagram of an internal configuration change detection environment is depicted in accordance with an illustrative embodiment. Rocket 100 in FIG. 1 is an example of an implementation for platform 200 in internal configuration change detection environment 202.

As depicted, optical internal configuration monitoring system 204 is associated with platform 200. When one component is "associated" with another component, the association is a physical association in the depicted examples. For example, a first component, optical internal configuration monitoring system 204, may be considered to be associated with a second component, platform 200, by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

In this illustrative example, optical internal configuration monitoring system 204 includes optical fiber system 206, light source 208, and detector 210. Optical fiber system 206 is configured to propagate light 212. The manner in which light 212 propagates through optical fiber system 206 changes as internal configuration 214 changes. In these illustrative examples, light source 208 generates light 212 and transmits light 212 through optical fiber system 206.

Detector 210 is configured to detect light 212 that propagates through optical fiber system 206. Further, detector 210 is configured to detect a change in the manner in which light 212 propagates through optical fiber system 206 when internal configuration 214 of platform 200 changes. As depicted, the changes in internal configuration 214 of platform 200 may include at least one of bending 216 of platform 200, twisting 218 of platform 200, as well as other changes in internal configuration 214 that may occur in platform 200.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C. In other examples, "at least one of" may be, for example, without limitation, two of item A, one of item B, and ten of item C; four of item B and seven of item C; and other suitable combinations.

Further, the monitoring for changes in internal configuration 214 may be performed in real-time by optical internal configuration monitoring system 204. In other words, the monitoring may be performed as quickly as light 212 can be sent through optical fiber system 206 and detected by detector 210.

Additionally, detector 210 may send information 220 to navigation system 222 in platform 200. With information 220, navigation system 222 may take into account changes in internal configuration 214 when guiding movement of platform 200. As a result, less compensation to the direction of movement of platform 200 may occur with the use of information 220.

Further, optical fiber system 206 in optical internal configuration monitoring system 204 may serve another purpose in addition to monitoring for changes to internal configuration 214 of platform 200. For example, devices 224 in network data processing system 226 in platform 200 may use optical fiber system 206. In other words, optical fiber system 206 may also function as communications links within network data processing system 226. Thus, devices 224 may transmit additional information 228 over optical fiber system 206 in addition to information 220. Information 220 and additional information 228 may be transmitted at the same time over optical fiber system 206 in these illustrative examples.

With the use of optical internal configuration monitoring system 204, less space and weight may be used to monitor for changes in internal configuration 214. For example, optical fiber system 206 may weigh less and use less space than gyroscopes and the associated attachments and isolation systems needed for gyroscopes.

Optical fiber system 206 may not require simulations and testing for placement locations in the manner that may be required for mechanical systems such as gyroscopes. As a result, the effort and expense needed to implement optical internal configuration monitoring system 204 may be less than currently used internal configuration detection systems.

Figure 3:
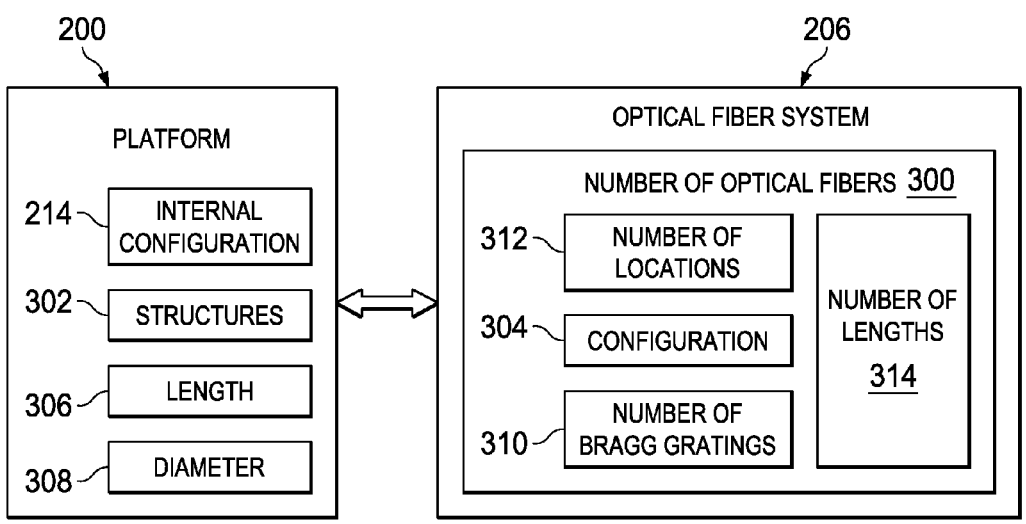
FIG. 3 is an illustration of a block diagram of an optical fiber system in accordance with an illustrative embodiment.

Turning now to FIG. 3, an illustration of a block diagram of an optical fiber system is depicted in accordance with an illustrative embodiment. Examples of components in optical fiber system 206 are shown in this figure.

As depicted, optical fiber system 206 is comprised of number of optical fibers 300. Number of optical fibers 300 may be comprised of different types of optical fibers. For example, number of optical fibers 300 may include at least one of glass optical fibers, plastic optical fibers, and other suitable types of optical fibers. Further, number of optical fibers 300 also may be located within a sheath or other protective cover to form an optical cable in which one or more of number of optical fibers 300 is present.

As illustrated, number of optical fibers 300 in optical fiber system 206 is associated with platform 200. Although platform 200 has been shown in the form of rocket 100 in FIG. 1, platform 200 may take other forms. For example, platform 200 may be selected from one of a mobile platform, a stationary platform, a land-based structure, an aquatic-based structure, a space-based structure, a launch vehicle, a missile, a rocket, a surface ship, a tank, a personnel carrier, a train, a spacecraft, a space station, a satellite, a submarine, an automobile, a power plant, a bridge, a dam, a manufacturing facility, a building, and/or other suitable platforms.

In these illustrative examples, number of optical fibers 300 may be associated with one or more of structures 302 in platform 200. Structures 302 may take various forms depending on the implementation for platform 200. For example, structures 302 may be a wall for a rocket booster, a wall for a fuel tank, a wing, a fin, a fuselage, and other suitable structures that may be present in platform 200. In these illustrative examples, number of optical fibers 300 may be associated with one or more of structures 302 in a number of different ways.

As depicted, number of optical fibers 300 may be connected to a structure in structures 302, attached to a structure in structures 302, placed within structures 302 during manufacturing of structures 302, placed within structures 302 when assembling structures 302, and in other suitable ways. For example, number of optical fibers 300 may be placed into layers of composite material forming the wall of a structure during manufacturing of that structure. These layers of composite material may then be cured with number of optical fibers 300 becoming an integral part of the structure in structures 302.

Thus, number of optical fibers 300 may be connected to platform 200. In other illustrative examples, number of optical fibers 300 may be formed as part of platform 200.

In these illustrative examples, configuration 304 of number of optical fibers 300 with respect to structures 302 in platform 200 may take a number of different forms. For example, configuration 304 of number of optical fibers 300 may be such that number of optical fibers 300 extends in a direction that is at least one of longitudinally along length 306 of platform 200, circumferentially around diameter 308 of platform 200, helically around diameter 308 of platform 200, or in some other manner with respect to platform 200.

Configuration 304 of number of optical fibers 300 is such that the manner in which light 212 in FIG. 2 propagates through number of optical fibers 300 changes when internal configuration 214 of platform 200 changes. With the use of number of optical fibers 300, less weight and space may be needed to monitor for changes in internal configuration 214 of platform 200.

In some illustrative examples, number of optical fibers 300 may include number of Bragg gratings 310. Each optical fiber in number of optical fibers 300 may have one or more of number of Bragg gratings 310.

Number of Bragg gratings 310 may be located in number of optical fibers 300 in number of locations 312. Number of locations 312 for number of Bragg gratings 310 may define number of lengths 314 within number of optical fibers 300.

In these illustrative examples, a Bragg grating in number of Bragg gratings 310 is configured to reflect one or more wavelengths in light 212 while allowing other wavelengths in light 212 in FIG. 2 to pass. In this manner, a change in internal configuration 214 for platform 200 may be identified along a length within number of lengths 314 through the use of number of Bragg gratings 310. In this manner, the use of number of Bragg gratings 310 in number of optical fibers 300 may provide a more accurate indication of where a change in internal configuration 214 of platform 200 occurs.

Figure 4:
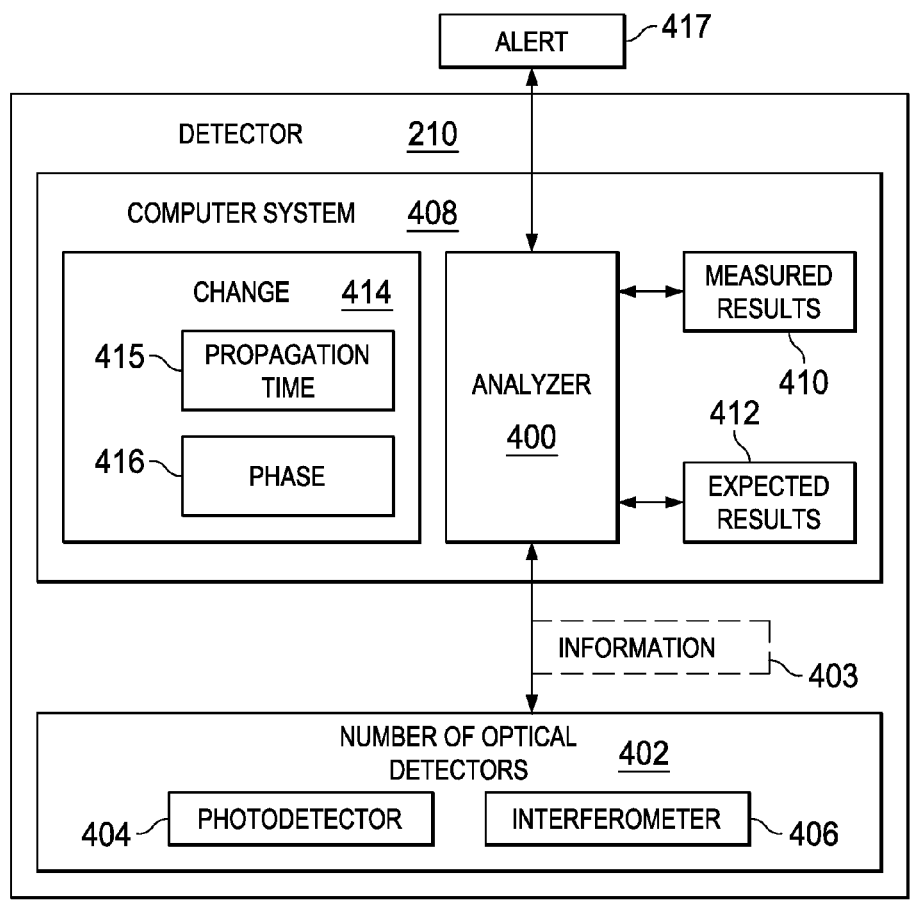
FIG. 4 is an illustration of a block diagram of a detector in accordance with an illustrative embodiment.

Turning now to FIG. 4, an illustration of a block diagram of a detector is depicted in accordance with an illustrative embodiment. Components that may be used in detector 210 are illustrated in this figure. Detector 210 takes the form of hardware and also may include software.

As illustrated, detector 210 includes analyzer 400 and number of optical detectors 402. Number of optical detectors 402 is connected to analyzer 400 and sends information 403 to analyzer 400.

In this illustrative example, number of optical detectors 402 may be implemented using various types of optical detectors. For example, number of optical detectors 402 may be implemented using at least one of photodetector 404, interferometer 406, and other suitable types of optical detectors.

Photodetector 404 is a hardware device configured to detect light 212 in FIG. 2 propagating through number of optical fibers 300 in FIG. 3 that reach photodetector 404. Photodetector 404 may be, for example, without limitation, a device selected from one of an active pixel sensor, a charged couple device, a photoresistor, a photodiode, and other suitable devices. Photodetector 404 may send information 403 in the form of an indication that light 212 has been detected. Information 403 also may include a timestamp in some illustrative examples.

Interferometer 406 is a hardware device. Interferometer 406 generates information about waves in light 212 to form information 403. For example, interferometer 406 may generate information 403 using light 212 as generated by light source 208 in FIG. 2 and light 212 detected after propagating light 212 through number of optical fibers 300. A comparison of light 212 generated by light source 208 and light 212 detected after propagating through number of optical fibers 300 may yield information about changes in the parameters of light 212. These changes may be changes in at least one of intensity, frequency, polarization, phase, and other changes in light 212. This information is sent to analyzer 400 in the form of information 403 as well as other types of information.

Analyzer 400 may be hardware, software, or a combination of the two. When software is used, the operations performed by analyzer 400 may be implemented in the program code configured to be run on a processor unit. When hardware is employed, the hardware may include circuits that operate to perform the operations in analyzer 400.

In the illustrative examples, the hardware may take the form of a circuit system, an integrated circuit, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. Additionally, the processes may be implemented in organic components integrated with inorganic components and/or may be comprised entirely of organic components excluding a human being. For example, the processes may be implemented as circuits in organic semiconductors.

For example, analyzer 400 may be implemented in computer system 408. Computer system 408 is comprised of one or more computers. When more than one computer is present, those computers may be in communication with each other via a communications medium such as a network. In this illustrative example, analyzer 400 receives information 403 and generates measured results 410 from information 403.

In some cases, information 403 may be measured results 410. In other examples, calculations, filtering, and other operations may be performed by analyzer 400 to obtain measured results 410 from information 403.

As depicted, analyzer 400 compares measured results 410 to expected results 412 to identify change 414. In this illustrative example, expected results 412 may be stored in a database. Expected results 412 may be results from sending light 212 through number of optical fibers 300 in optical fiber system 206 in FIG. 2. In other words, measured results 410 identified when internal configuration 214 in FIG. 2 has not changed may be stored to form expected results 412.

In these illustrative examples, change 414 is a change to the manner in which light 212 propagates through number of optical fibers 300. Change 414 may be used to identify when internal configuration 214 of platform 200 changes. In these illustrative examples, change 414 may be selected from at least one of a change in propagation time 415 and a change in phase 416.

Alert 417 may be generated by analyzer 400 when change 414 is present. For example, alert 417 may be generated when change 414 is identified as being greater than a threshold. In another example, alert 417 also may be generated if change 414 has a particular frequency, lasts for a selected period of time, or has some other characteristic suitable for generating alert 417.

Alert 417 may be, for example, without limitation, a message that is sent to navigation system 222 in FIG. 2 or some other system or device within platform 200. Alert 417 may include information used by navigation system 222 in making adjustments to the direction in which platform 200 travels.

Figure 5:
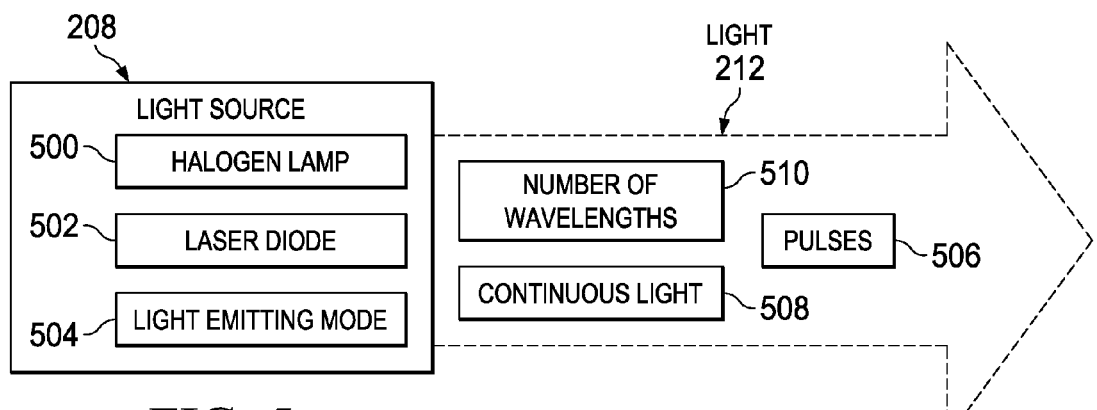
FIG. 5 is an illustration of a block diagram of a light source in accordance with an illustrative embodiment.

In FIG. 5, an illustration of a block diagram of a light source is depicted in accordance with an illustrative embodiment. Examples of components that may be used to implement light source 208 in FIG. 2 are illustrated in this figure.

As depicted, light source 208 generates light 212. Light source 208 may be implemented using a number of different hardware devices. For example, light source 208 may be implemented using at least one of halogen lamp 500, laser diode 502, light emitting diode 504, and other suitable devices that may be used to generate light 212.

In these illustrative examples, light source 208 is configured to generate light 212 such that light 212 may be in the form of pulses 506. These pulses may have different durations depending on the particular implementation. In some cases, light 212 may be generated in the form of continuous light 508. Further, light 212 may be generated by light source 208 to have number of wavelengths 510.

The illustration of internal configuration change detection environment 202 and the components illustrated in FIGS. 2-5 are not meant to imply physical or architectural limitations the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, in some illustrative examples, components for light source 208 may be implemented in the same blocks as components for detector 210 in FIG. 2. For example, when interferometer 406 is used to implement number of optical detectors 402 in detector 210, interferometer 406 also may include light source 208. As another example, number of optical fibers 300 may be continuous or segmented depending on the particular implementation.

Figure 6:
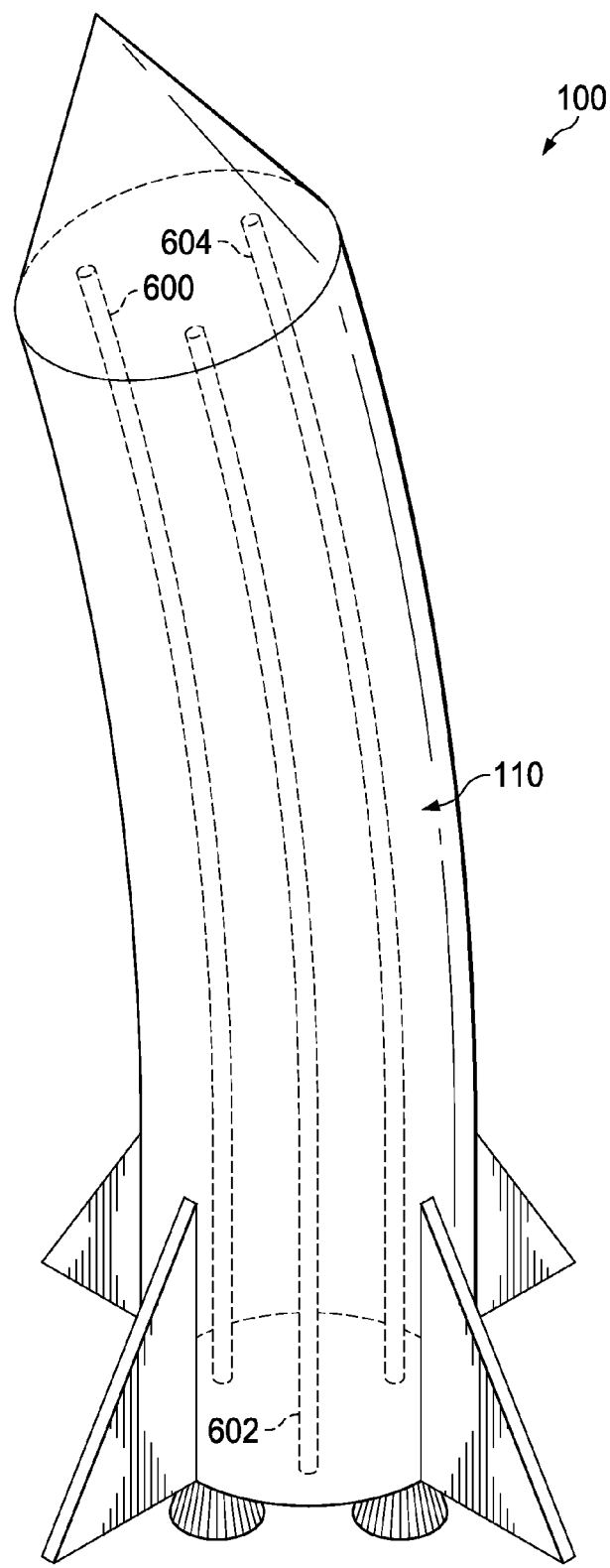
FIG. 6 is an illustration of a rocket with an internal configuration change in accordance with an illustrative embodiment.

Turning now to FIG. 6, an illustration of a rocket with an internal configuration change is depicted in accordance with an illustrative embodiment. Rocket 100 from FIG. 1 is shown in this figure with an internal configuration change in the form of a bend. This bend is exaggerated for purposes of illustrating features of an illustrative embodiment and not representative of an actual amount of bending that may occur in an internal configuration change of rocket 100.

In this illustrative example, optical fiber 600, optical fiber 602, and optical fiber 604 are illustrated in optical fibers 110. Optical fiber 604 has a greater amount of bending as compared to optical fiber 600 and optical fiber 602. As a result, the manner in which light propagates through optical fiber 604 may change more than the manner in which light propagates through optical fiber 600 and optical fiber 602.

The differences in the amount of change in the manner in which light propagates through an optical fiber in optical fibers 110 may be used to identify an occurrence of a change in the internal configuration of rocket 100. For example, compression or stretching of optical fiber 600 will change the manner in which light propagates through optical fiber 600. This change may indicate a change in the internal configuration of rocket 100. In these illustrative examples, a compression or stretching of an optical fiber occurs when the internal configuration of rocket 100 changes. This compression or stretching of the optical fiber causes a change in the manner in which light propagates through it.

Further, the difference in the changes in the manner in which light propagates through optical fiber 600, optical fiber 602, and optical fiber 604 also may be used to identify the manner in which the bending occurs. For example, the change in the manner in which light propagates through optical fiber 602 may be different than the change in the manner in which light propagates through optical fiber 600. In other words, internal configuration changes may be detected by measuring changes to the manner in which light propagates through a single optical fiber, or by comparing the changes of one optical fiber to another optical fiber.

In these illustrative examples, the light that propagates through optical fibers 110 may change as a result of the bending in rocket 100 for a number of different reasons. For example, the bending may stretch or compress optical fibers 110 such that the length of optical fibers 110 changes. In another example, the fact that optical fibers 110 are bent rather than substantially straight also may change the manner in which light propagates through optical fibers 110.

Figure 7:
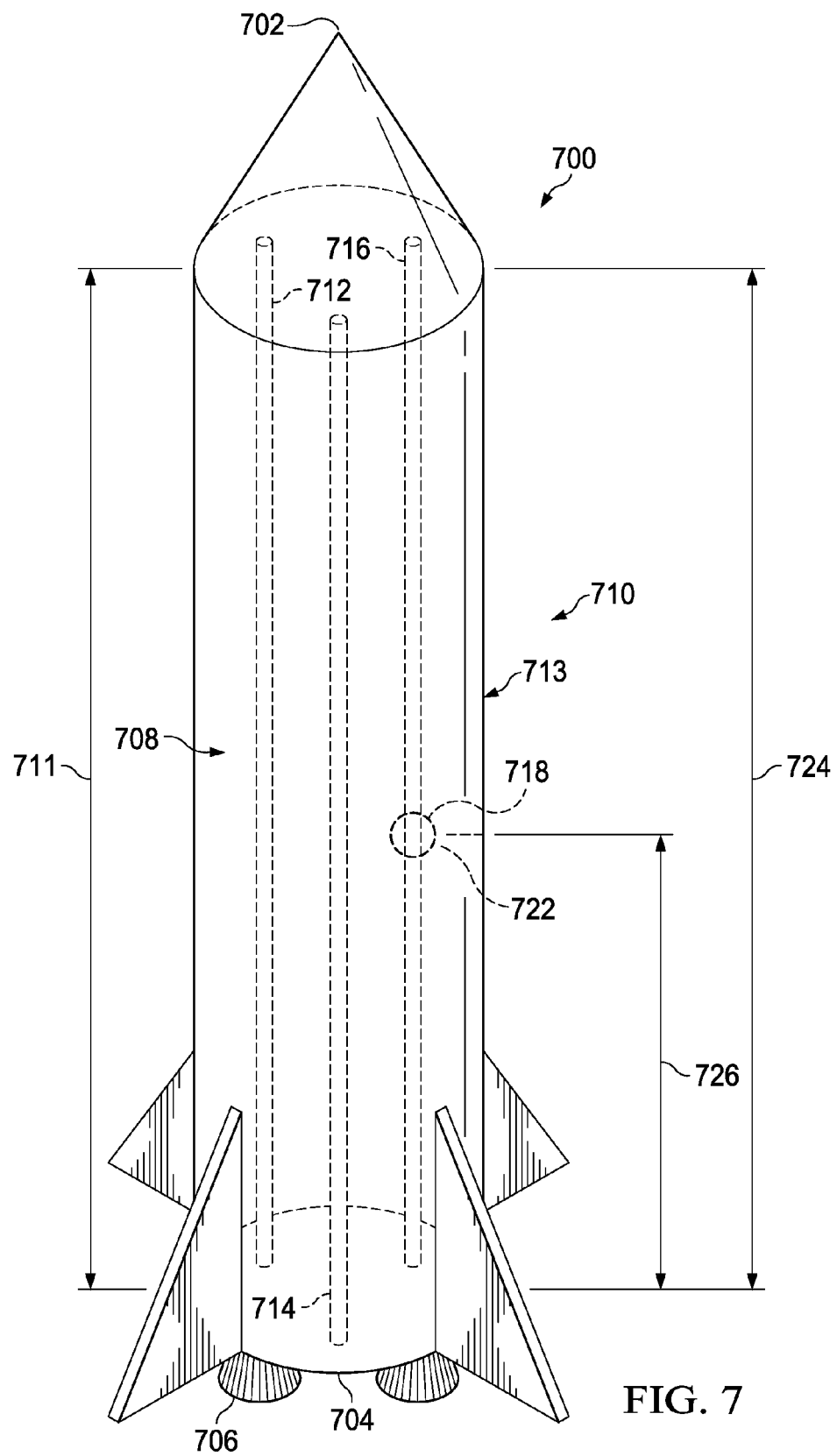
FIG. 7 is an illustration of a platform with an optical internal configuration monitoring system in accordance with an illustrative embodiment.

Turning now to FIG. 7, an illustration of a platform with an optical internal configuration monitoring system is depicted in accordance with an illustrative embodiment. This optical internal configuration monitoring system is an example of one implementation for optical internal configuration monitoring system 204 shown in block form in FIG. 2.

In this illustrative example, rocket 700 is an example of one implementation for platform 200 in FIG. 2. Rocket 700 has first end 702 and second end 704. Rocket engines 706 are located at second end 704.

Additionally, rocket 700 includes optical fibers 708, which are part of optical internal configuration monitoring system 710. Optical internal configuration monitoring system 710 is an example of an implementation for optical internal configuration monitoring system 204 shown in block form in FIG. 2. Optical fibers 708 extend longitudinally along length 711 of rocket 700.

As depicted, optical fiber 712, optical fiber 714, and optical fiber 716 are shown as being associated with structure 713 of rocket 700. In this illustrative example, optical fiber 716 includes Bragg grating 718 at location 722 along the length of optical fibers 708. As a result, optical fiber 716 may be divided into length 724 and length 726.

Light passing through Bragg grating 718 travels through length 724 of optical fiber 716. This light may be used to identify a bend along length 724 of optical fiber 716. Light reflected by Bragg grating 718 may be used to identify changes in the manner in which light propagates through optical fiber 716 along length 726. Length 726 is a shorter length than length 724. The identification of a change in the propagation of light along length 726 may be used to more precisely identify where a bend may occur. This precision may increase by including additional Bragg gratings in optical fiber 716.

Although not shown, optical fiber 712 and optical fiber 714 also may include one or more Bragg gratings depending on the particular implementation. Further, additional optical fibers with or without Bragg gratings also may be present, but not seen in optical fibers 708 as depicted in this view of rocket 700.

Turning now to FIG. 8, an illustration of components that may be used in an optical internal configuration monitoring system is depicted in accordance with an illustrative embodiment. In this illustrative example, optical internal configuration monitoring system 800 is an example of a system comprising components that may be used to implement optical internal configuration monitoring system 204 in FIG. 2.

As illustrated, optical internal configuration monitoring system 800 includes laser source 802, detector 804, detector 806, optical fiber 808, and Bragg gratings 810. These different components are examples of components that may be used to detect changes in the internal configuration of a platform, such as rocket 100 in FIG. 1.

Laser source 802 is configured to generate coherent light and send the coherent light through first end 812 of optical fiber 808. Detector 804 is configured to detect the coherent light sent through optical fiber 808 at second end 814. Detector 806 is configured to detect reflections of the coherent light caused by Bragg gratings 810.

In this illustrative example, Bragg gratings 810 include Bragg gratings 816, 818, 820, 822, 824, 826, 828, and 830. In these illustrative examples, Bragg gratings 810 are periodic structures in this illustrative example. In the illustrative examples, a periodic structure is a material parameter change whose change is periodic with respect to physical displacement in that material. In the case of a Bragg grating, the material parameter is the refractive index and that index value will vary periodically with the length of the optical fiber within the area containing the grating. In other words, Bragg gratings 810 are spaced periodically in these depicted examples. Bragg gratings 810 may be index gratings, located within optical fiber 808.

The arrangement of Bragg gratings 810 is designed to select a small portion of coherent light at a wavelength proportional to the grating spacing such that most of the coherent light continues through the optical fiber. For example, Bragg grating 816 may select a small portion of coherent light traveling through optical fiber 808. The portion of coherent light selected by Bragg grating 816 is reflected back towards detector 806 in this illustrative example. Other Bragg gratings in Bragg gratings 810 along optical fiber 808 may select different wavelengths of light traveling through optical fiber 808 to be reflected back to detector 806.

As depicted, a return pulse of coherent light reflected by Bragg grating 816 may arrive at a different time than a return pulse of coherent light by Bragg grating 818. These return pulses arrive at different times such that these times for the return pulses correlate to the portion of optical fiber 808 that the return pulse has traversed. As a result, information about different Bragg gratings along optical fiber 808 may be detected.

In the illustrative examples, harmonics in the optical signals may originate either from actual mechanical harmonic motion in the rocket structure or from signals generated directly in the optical fiber itself. In either case, these harmonics can be ignored.

In the case of mechanical motions, these motions will be at frequencies much higher than the fundamental rocket motions. For example, these frequencies of the mechanical motions may be two times, three times, or some other number of times higher than the frequencies of fundamental rocket motions. As such, if such signals are detected, they can be removed through electronic circuitry at the detector, or computationally removed by a signal analysis system. Optical harmonics, which may be generated in the fiber, may be simply removed with optical filters that transmit signals at the optical source, but are opaque at the optical harmonics.

Turning now to FIG. 9, another illustration of a rocket with an optical internal configuration monitoring system is depicted in accordance with an illustrative embodiment. In this illustrative example, rocket 900 is an example of one implementation for platform 200 in FIG. 2. Rocket 900 has first end 902 and second end 904. Rocket engines 906 are located at second end 904.

Additionally, rocket 900 includes optical fibers 908, which are part of optical internal configuration monitoring system 910. Optical internal configuration monitoring system 910 is an example of an implementation for optical internal configuration monitoring system 204 shown in block form in FIG. 2. Optical fibers 908 extend circumferentially around diameter 912 of rocket 900.

As can be seen in this illustrative example, optical fibers 908 include optical fibers 914, 916, 918, 920, 922, and 924. Although optical fibers 908 are depicted as a complete circle, each of optical fibers 908 includes an entrance and an exit with an accompanying light source and detector (not shown in this illustration). The light source may be located on one end of each optical fiber, while the detector may be located on the opposite end of the optical fiber.

As depicted, the configuration of these optical fibers may be used to detect twisting of rocket 900. In particular, this twisting may occur around axis 926 extending centrally through rocket 900. Twists which occur within rocket 900 will cause some fibers in optical fibers 908 to lengthen more than other fibers in optical fibers 908. The change in the manner in which light propagates through the fibers in optical fibers 908 may detect the twisting in rocket 900.

In other illustrative examples, each of optical fibers 914, 916, 918, 920, 922, and 924 may contain more than one light source. For example, optical fiber 914 may have one light source on each end of optical fiber 914.

When twisting of rocket 900 occurs, light traveling in one direction along optical fiber 914 may experience a longer path length than light traveling in the other direction along optical fiber 914. These differences provide information about the twisting of rocket 900.

Figure 10:
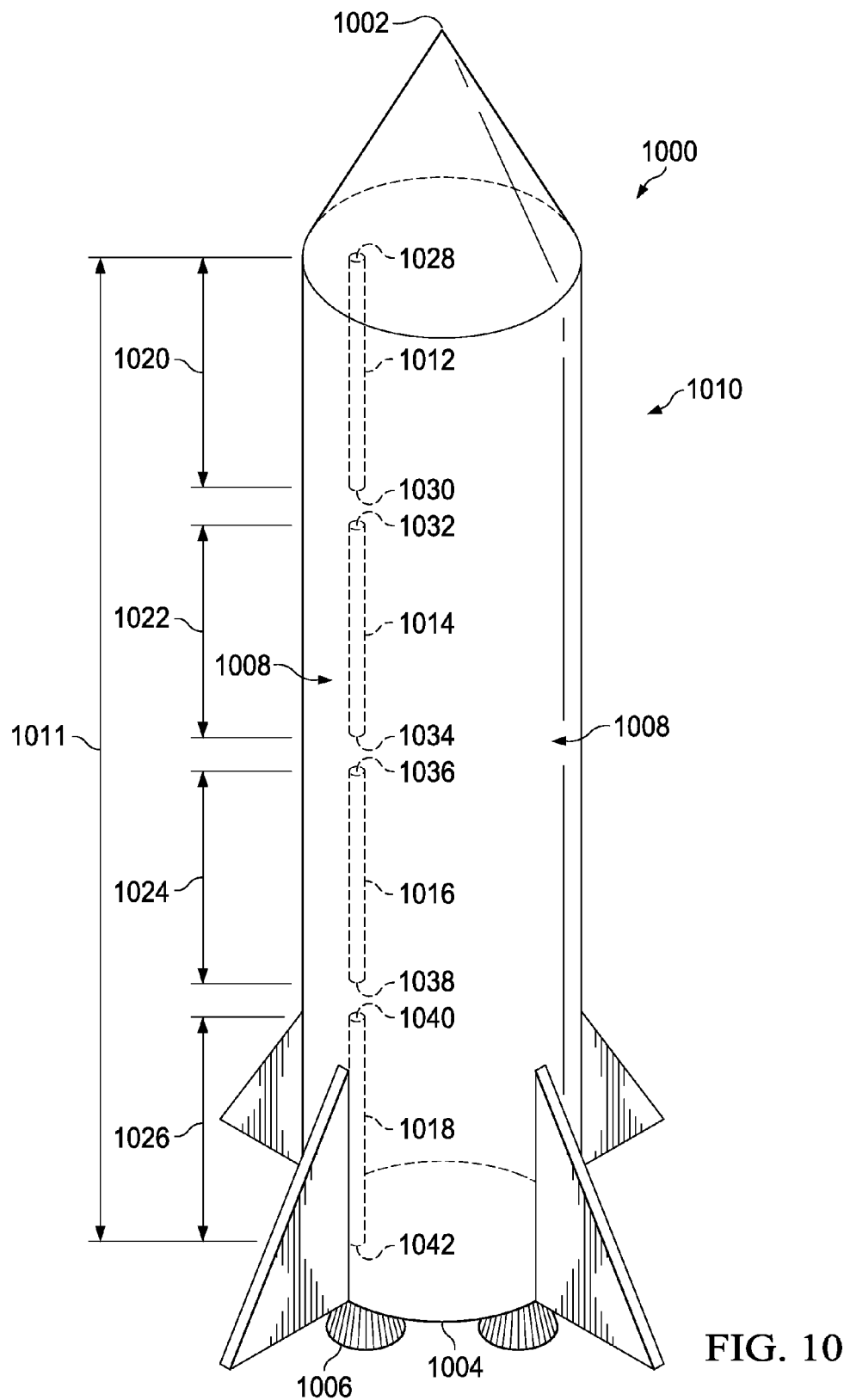
FIG. 10 is another illustration of a rocket with an optical internal configuration monitoring system in accordance with an illustrative embodiment.

Turning now to FIG. 10, another illustration of a rocket with an optical internal configuration monitoring system is depicted in accordance with an illustrative embodiment. This optical internal configuration monitoring system is an example of one implementation for optical internal configuration monitoring system 204 shown in block form in FIG. 2.

In this illustrative example, rocket 1000 is an example of one implementation for platform 200 in FIG. 2. Rocket 1000 has first end 1002 and second end 1004. Rocket engines 1006 are located at second end 1004.

As depicted, rocket 1000 includes optical fibers 1008 which are part of optical internal configuration monitoring system 1010. Optical fibers 1008 extend longitudinally along length 1011 of rocket 1000.

Optical fibers 1008 are segmented in this illustrative example. As illustrated, optical fibers 1008 include optical fiber 1012, optical fiber 1014, optical fiber 1016, and optical fiber 1018. Optical fiber 1012, optical fiber 1014, optical fiber 1016, and optical fiber 1018 extend longitudinally along length 1020, length 1022, length 1024, and length 1026, respectively.

In these illustrative examples, each optical fiber in optical fibers 1008 may provide information specific to that optical fiber. For example, optical fiber 1012 may provide information about changes in the manner in which light propagates through optical fiber 1012 along length 1020 of rocket 1000. Similarly, optical fiber 1014, optical fiber 1016, and optical fiber 1018 provide information about changes in the manner in which light propagates through length 1022, length 1024, and length 1026 of rocket 1000, respectively.

Each of the optical fibers in optical fibers 1008 includes a light source and a detector in these illustrative examples. For example, optical fiber 1012 includes light source 1028 and detector 1030; optical fiber 1014 includes light source 1032 and detector 1034; optical fiber 1016 includes light source 1036 and detector 1038; and optical fiber 1018 includes light source 1040 and detector 1042. Detector 1030, detector 1034, detector 1038, and detector 1042 provide information about the manner in which light propagates through optical fibers 1012, 1014, 1016, and 1018, respectively. This information may be transmitted to a navigation system, such as navigation system 222 in FIG. 2.

In other illustrative examples, an optical relay may take the light from the end of each fiber and focus the light into the next fiber. This optical relay may be a lens or some other type of relay device. For example, light from light source 1028 is transmitted along length 1020 of optical fiber 1012. An optical relay takes the light from the end of optical fiber 1012 and focuses the light into optical fiber 1014. In this manner, changes in the manner in which light propagates along length 1011 of rocket 1000 may be detected. Thus, less light sources may be needed. For example, one or two light sources may be used in place of the ones illustrated when optical relays are employed. For example, light source 1032, light source 1036, and light source 1040 are not needed. Detector 1030, detector 1034, and detector 1038 may or may not be present in these illustrative examples.

In another illustrative example, light from light source 1028 is transmitted along length 1020 of optical fiber 1012 to detector 1030. As depicted, detector 1030 measures the intensity of the light and light source 1032 transmits light with identical characteristics to the light measured by detector 1030 along length 1022 of optical fiber 1016. Detector 1034 measures the intensity of the light propagating along optical fiber 1014 and light source 1036 transmits light with substantially identical characteristics to the light measured by detector 1034 along length 1024 of optical fiber 1016. Similarly, detector 1038 measures the intensity of the light propagating along optical fiber 1016 and light source 1040 transmits light with identical characteristics to the light measured by detector 1038. Detector 1038 measures the intensity of light propagating through optical fiber 1018. In this manner, the segments in optical fibers 1008 may simulate one long fiber extending longitudinally along length 1011 of rocket 1000.

Figure 11:
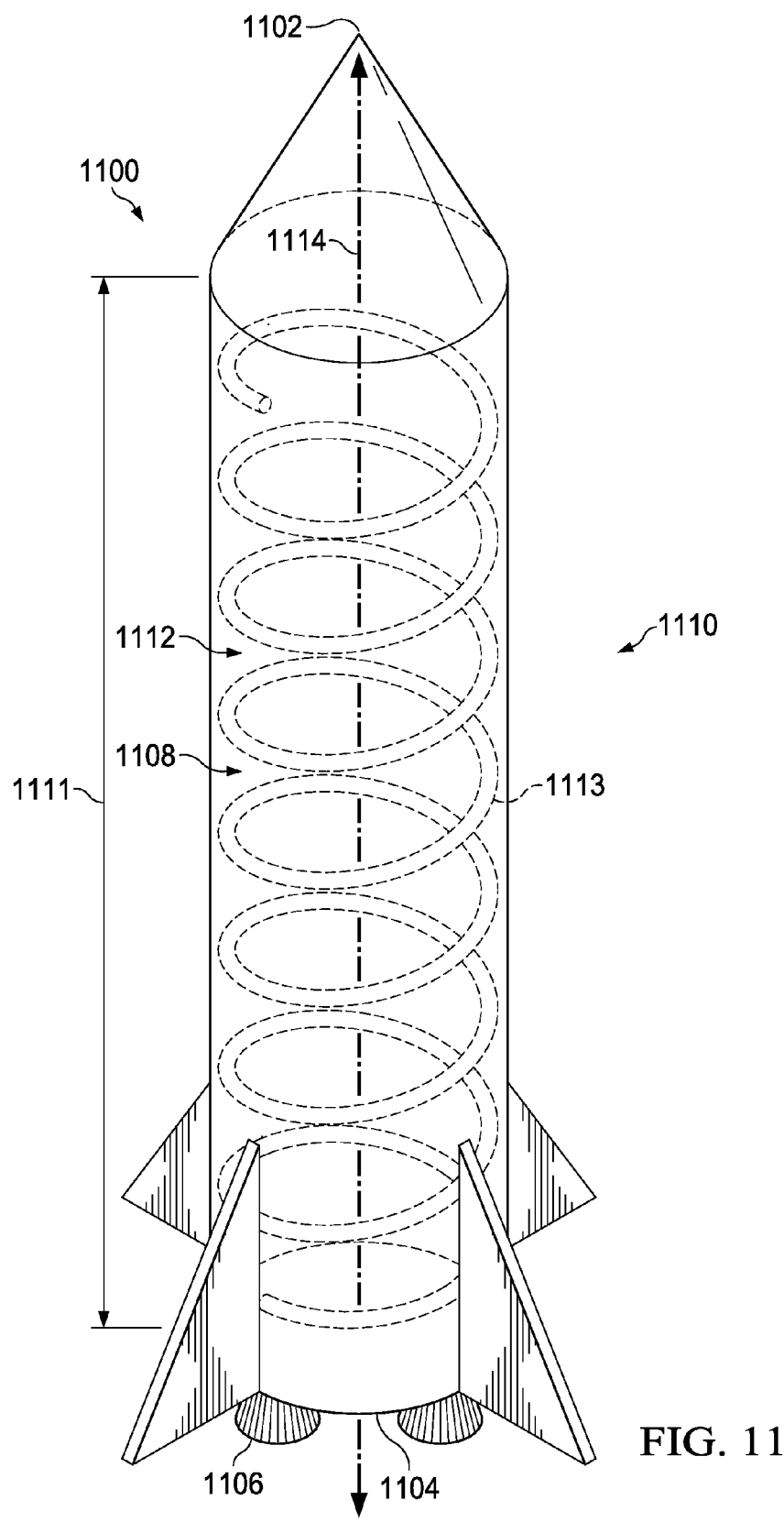
FIG. 11 is another illustration of a rocket with an optical internal configuration monitoring system in accordance with an illustrative embodiment.

Turning now to FIG. 11, another illustration of a rocket with an optical internal configuration monitoring system is depicted in accordance with an illustrative embodiment. This optical internal configuration monitoring system is an example of one implementation for optical internal configuration monitoring system 204 shown in block form in FIG. 2.

In this illustrative example, rocket 1100 is an example of one implementation for platform 200 in FIG. 2. Rocket 1100 has first end 1102 and second end 1104. Rocket engines 1106 are located at second end 1104.

As depicted, rocket 1100 includes optical fiber system 1108 which is part of optical internal configuration monitoring system 1110. In this illustrative example, optical fiber system 1108 extends helically along length 1111 of rocket 1100.

Optical fiber system 1108 has a configuration of helix 1112 in this illustrative example. Helix 1112 may be formed using a single optical fiber or multiple optical fibers. As depicted, optical fiber system 1108 is comprised of optical fiber 1113 within helix 1112. Optical fiber 1113 extends helically around the diameter of rocket 1100 along axis 1114 extending centrally through rocket 1100.

In this illustrative example, the configuration of optical fiber 1113 in helix 1112 allows for the simultaneous measurement of length and twist configuration changes in rocket 1100. In some illustrative examples, rocket 1100 may include one or more helixes in addition to helix 1112.

A light source for optical fiber system 1108 in helix 1112 may be located on first end 1102 or second end 1104. Similarly, a detector for optical fiber system 1108 in helix 1112 may be located on first end 1102 or second end 1104. When helix 1112 is a segmented helix, a light source and a detector may be present for each segment in helix 1112.

Figure 12:
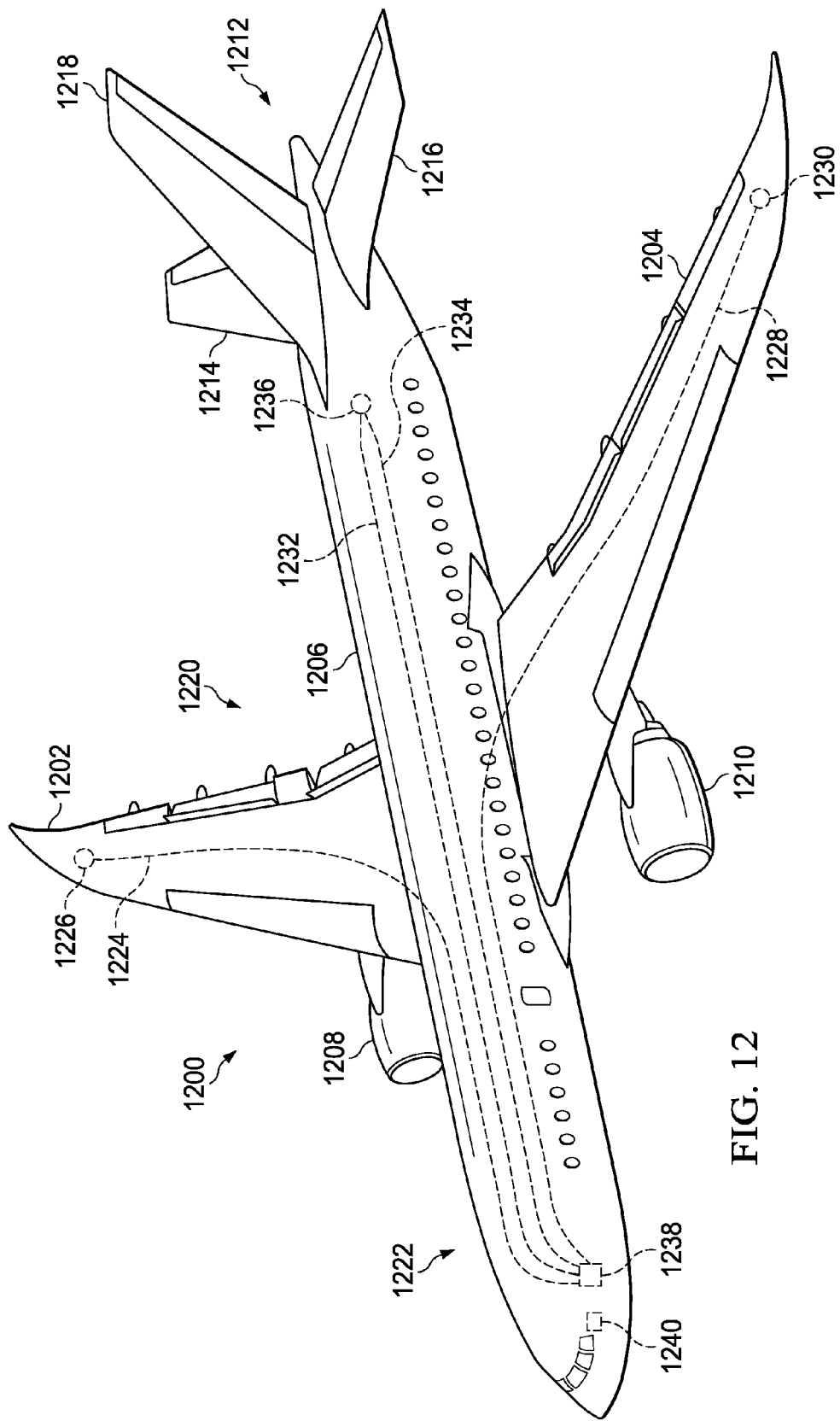
FIG. 12 is an illustration of an aircraft in which an optical internal configuration monitoring system may be implemented accordance with an illustrative embodiment.

With reference now to FIG. 12, an illustration of an aircraft in which an optical internal configuration monitoring system may be implemented is depicted in accordance with an illustrative embodiment. In this illustrative example, aircraft 1200 has wing 1202 and wing 1204 attached to body 1206. Aircraft 1200 includes engine 1208 attached to wing 1202 and engine 1210 attached to wing 1204.

Body 1206 has tail section 1212. Horizontal stabilizer 1214, horizontal stabilizer 1216, and vertical stabilizer 1218 are attached to tail section 1212 of body 1206.

Aircraft 1200 is an example of an aircraft in which an optical internal configuration monitoring system 1220 may be implemented. In this illustrative example, optical fiber system 1222 extends through body 1206, wing 1202, and wing 1204. Optical fiber 1224 is connected to light source 1226. Optical fiber 1228 is connected to light source 1230. Optical fiber 1232 and optical fiber 1234 are connected to light source 1236. Each of these optical fibers is connected to detector 1238.

Information about light transmitted through optical fibers 1224, 1228, 1232, and 1234, and detected by detector 1238 may be sent to health monitoring system 1240. Health monitoring system 1240 may determine whether configuration changes in body 1206, wing 1202, and wing 1204 are changes that are expected during operation of aircraft 1200. Changes that are not expected may be recorded and alerts may be generated as needed. In this manner, real time monitoring of changes in aircraft 1200 may be performed.

Further, other illustrative examples may be implemented in other types of platforms other than rocket 100 in FIG. 1 and aircraft 1200 in FIG. 12. In other illustrative examples, the configurations of optical fibers in FIGS. 6-11 may be used in other platforms other than a rocket. For example, an optical internal configuration monitoring system, such as optical internal configuration monitoring system 204 in FIG. 2, may be used to provide real-time feedback on the internal configuration of an airframe for an aircraft. Of course, an optical internal configuration monitoring system may be used for other structures other than an airframe and a rocket as discussed above.

The different components shown in FIG. 1 and FIGS. 6-11 may be combined with components in FIGS. 2-5, used with components in FIG. 2-5, or a combination of the two. Additionally, some of the components in FIG. 1 and FIGS. 6-11 may be illustrative examples of how components shown in block form in FIG. 2-5 can be implemented as physical structures.

Figure 13:
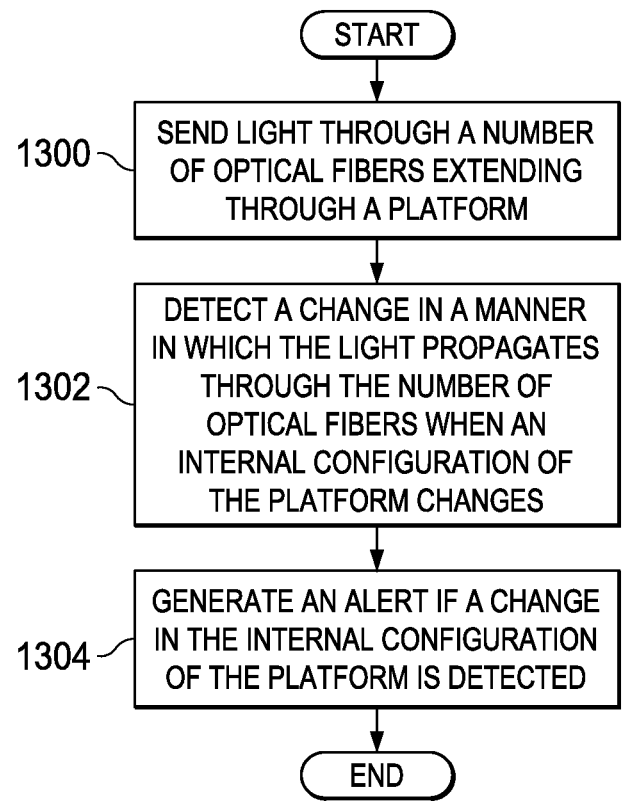
FIG. 13 is an illustration of a flowchart of a process for detecting a change in an internal configuration of a platform in accordance with an illustrative embodiment.

Turning now to FIG. 13, an illustration of a flowchart of a process for detecting a change in an internal configuration of a platform is depicted in accordance with an illustrative embodiment. The process illustrated in FIG. 13 may be implemented in optical internal configuration monitoring system 204 in FIG. 2.

The process begins by sending light through a number of optical fibers extending through a platform (operation 1300). This light may be sent from a light source, such as light source 208 in FIG. 2. The process then detects a change in a manner in which the light propagates through the number of optical fibers when an internal configuration of the platform changes (operation 1302). The change may be any change in the internal configuration of the platform, a change that exceeds a threshold, a change having a particular frequency, a change that occurs for more than some period of time, or some other change in the internal configuration of the platform.

Next, an alert is generated if a change in the internal configuration of the platform is detected (operation 1304), with the process terminating thereafter. This alert may be alert 417 sent by analyzer 400 in FIG. 4 to a navigation system such as navigation system 222 in FIG. 2, to a health monitoring system such as health monitoring system 1240 in FIG. 12, or to some other suitable system or device. In some illustrative examples, this alert may indicate that an operation, such as termination of flight, is necessary for the safe operation of a platform, such as a rocket. In other illustrative examples, the alert may indicate a configuration change that may be monitored by navigation system 222. In this manner, the process illustrated in FIG. 13 may provide continuous feedback to navigation system 222 to aid in control of the rocket. Further, this information also may be used to abort a mission for a rocket when needed.

The flowchart and block diagrams in the different depicted embodiments illustrate the architecture, functionality, and operation of some possible implementations of apparatuses, methods, and computer program products. In this regard, each block in the flowchart or block diagrams may represent a module, segment, or portion of computer usable or readable program code, which comprises one or more executable instructions for implementing the specified function or functions. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

Turning now to FIG. 14, an illustration of a data processing system is depicted in accordance with an illustrative embodiment. Data processing system 1400 may be used to implement one or more computers in computer system 408 in FIG. 4, navigation system 222, and/or network data processing system 226 in FIG. 2.

In this illustrative example, data processing system 1400 includes communications framework 1402, which provides communications between processor unit 1404, memory 1406, persistent storage 1408, communications unit 1410, input/output (I/O) unit 1412, and display 1414. In this example, communication framework may take the form of a bus system.

Processor unit 1404 serves to execute instructions for software that may be loaded into memory 1406. Processor unit 1404 may be a number of processors, a multi-processor core, or some other type of processor, depending on the particular implementation.

Memory 1406 and persistent storage 1408 are examples of storage devices 1416. A storage device is any piece of hardware that is capable of storing information, such as, for example, without limitation, data, program code in functional form, and/or other suitable information either on a temporary basis and/or a permanent basis. Storage devices 1416 may also be referred to as computer readable storage devices in these illustrative examples. Memory 1406, in these examples, may be, for example, a random access memory or any other suitable volatile or non-volatile storage device. Persistent storage 1408 may take various forms, depending on the particular implementation.

For example, persistent storage 1408 may contain one or more components or devices. For example, persistent storage 1408 may be a hard drive, a flash memory, a rewritable optical disk, a rewritable magnetic tape, or some combination of the above. The media used by persistent storage 1408 also may be removable. For example, a removable hard drive may be used for persistent storage 1408.

Communications unit 1410, in these illustrative examples, provides for communications with other data processing systems or devices. In these illustrative examples, communications unit 1410 is a network interface card.

Input/output unit 1412 allows for input and output of data with other devices that may be connected to data processing system 1400. For example, input/output unit 1412 may provide a connection for user input through a keyboard, a mouse, and/or some other suitable input device. Further, input/output unit 1412 may send output to a printer. Display 1414 provides a mechanism to display information to a user.

Instructions for the operating system, applications, and/or programs may be located in storage devices 1416, which are in communication with processor unit 1404 through communications framework 1402. The processes of the different embodiments may be performed by processor unit 1404 using computer-implemented instructions, which may be located in a memory, such as memory 1406.

These instructions are referred to as program code, computer usable program code, or computer readable program code that may be read and executed by a processor in processor unit 1404. The program code in the different embodiments may be embodied on different physical or computer readable storage media, such as memory 1406 or persistent storage 1408.

Program code 1418 is located in a functional form on computer readable media 1420 that is selectively removable and may be loaded onto or transferred to data processing system 1400 for execution by processor unit 1404. Program code 1418 and computer readable media 1420 form computer program product 1422 in these illustrative examples. In one example, computer readable media 1420 may be computer readable storage media 1424 or computer readable signal media 1426.

In these illustrative examples, computer readable storage media 1424 is a physical or tangible storage device used to store program code 1418 rather than a medium that propagates or transmits program code 1418.

Alternatively, program code 1418 may be transferred to data processing system 1400 using computer readable signal media 1426. Computer readable signal media 1426 may be, for example, a propagated data signal containing program code 1418. For example, computer readable signal media 1426 may be an electromagnetic signal, an optical signal, and/or any other suitable type of signal. These signals may be transmitted over communications links, such as wireless communications links, optical fiber cable, coaxial cable, a wire, and/or any other suitable type of communications link.

The different components illustrated for data processing system 1400 are not meant to provide architectural limitations to the manner in which different embodiments may be implemented. The different illustrative embodiments may be implemented in a data processing system including components in addition to and/or in place of those illustrated for data processing system 1400. Other components shown in FIG. 14 can be varied from the illustrative examples shown. The different embodiments may be implemented using any hardware device or system capable of running program code 1418.

Thus, the illustrative embodiments provide a method and apparatus for monitoring a platform for changes in the internal configuration of the platform. In the illustrative examples, a number of optical fibers extend through the platform. As described above, the number of optical fibers may be associated with the platform by being at least one of connected to the platform, embedded within the platform, formed as part of platform, and associated with the platform in other suitable ways. A detector is configured to detect a change in the manner in which light propagates through the optical fibers when an internal configuration of the platform changes.

An alert may be generated when the change in the platform is detected. The nature of this alert may be a measurement of bending magnitude and rate of bend in the pitch and yaw axes. This alert may also take the form of other information to control operation of the platform. This alert may be used by other components in the platform such as a navigation system. The navigation system may take into account the change in the internal configuration of the platform to reduce adjustments that may be made to the direction in which the platform changes. As a result, fewer corrections and over-corrections may occur.

In these illustrative examples, optical internal configuration monitoring system 204 is lighter than, and takes up less space than, currently used internal configuration detection systems. Additionally, the amount of time and expense needed to design an optical internal configuration monitoring system for a platform is reduced because simulations and testing to identify locations for gyroscopes and connection systems for gyroscopes may be avoided.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
a number of optical fibers extending through a platform;
a detector configured to detect a change to an internal configuration of the platform by determining a change in a manner in which light propagates through the number of optical fibers to identify a bending of the platform; and
a navigation system configured to account for the bending of the platform to avoid unnecessary corrections to the direction in which the platform travels.

2. The apparatus of claim 1, wherein the detector is further configured to transmit information about the change in the manner in which the light propagates through the number of optical fibers to a navigation system for the platform.

3. The apparatus of claim 1, wherein the change in the internal configuration of the platform is selected from at least one of a bending of the platform and a twisting of the platform.

4. The apparatus of claim 1, wherein the change in the manner in which the light propagates through the number of optical fibers is selected from at least one of a change in propagation time and a change in phase.

5. The apparatus of claim 1, wherein the number of optical fibers is formed within a fuselage of the platform.

6. The apparatus of claim 1, wherein the number of optical fibers is attached to the platform.

7. The apparatus of claim 1, wherein the platform is a rocket and wherein the number of optical fibers is configured to extend at least one of longitudinally along a length of the rocket, helically around a diameter of the rocket, and circumferentially around the diameter of the rocket.

8. The apparatus of claim 1 further comprising:
a light source configured to send the light through the number of optical fibers.

9. The apparatus of claim 8, wherein the light source is configured to transmit pulses of coherent light.

10. The apparatus of claim 8, wherein the light source is configured to send pulses of the light through the number of optical fibers.

11. The apparatus of claim 8, wherein the light source is configured to send the light using a number of wavelengths.

12. The apparatus of claim 1, wherein a number of Bragg gratings is present in the number of optical fibers.

13. The apparatus of claim 12, wherein the number of Bragg gratings is in a number of locations in the number of optical fibers, wherein the number of locations defines a number of lengths along which the change in the internal configuration of the platform is monitored.

14. The apparatus of claim 1 further comprising:
a number of devices configured to transmit information used to operate the platform using the number of optical fibers.

15. The apparatus of claim 1, wherein the platform is selected from one of a mobile platform, a stationary platform, a land-based structure, an aquatic-based structure, a space-based structure, a launch vehicle, a missile, a rocket, a surface ship, a tank, a personnel carrier, a train, a spacecraft, a space station, a satellite, a submarine, an automobile, a power plant, a bridge, a dam, a manufacturing facility, and a building.

16. The apparatus of claim 1 further comprising:
the detector configured to generate an alert based on a bending magnitude and rate of bend in pitch and yaw axes of the platform; and
a navigation system configured to use the alert to account for the change to the internal configuration of the platform to reduce adjustments made to a direction in which the platform changes and reduce corrections and over-corrections.

17. A method for detecting a change in an internal configuration of a platform, the method comprising:
sending light through a number of optical fibers extending through the platform;
detecting a deformation of the platform by determining a change in a manner in which the light propagates through the number of optical fibers when the internal configuration of the platform changes to identify a bending of the platform; and
accounting for the bending of the platform to avoid unnecessary corrections to the direction in which the platform travels.

18. The method of claim 17, wherein a detector is configured to send information about the change in the manner in which the light propagates through the number of optical fibers to a navigation system for the platform.

19. The method of claim 17, wherein the change in the internal configuration of the platform is selected from at least one of a bending of the platform and a twisting of the platform.

20. The method of claim 17, wherein the change in the manner in which the light propagates through the number of optical fibers is selected from at least one of a change in propagation time and a change in phase.

21. The method of claim 17, wherein a number of Bragg gratings is in a number of locations in the number of optical fibers, wherein the number of locations defines a number of lengths along which the change in the internal configuration of the platform is monitored.

* * * * *